(12) United States Patent
Franke et al.

(10) Patent No.: US 7,056,313 B2
(45) Date of Patent: Jun. 6, 2006

(54) AESTHETICALLY IMPROVED SIDE PANELS FOR DISPOSABLE GARMENT AND METHODS OF MAKING THE SAME

(75) Inventors: Mark S. Franke, Neenah, WI (US); Cynthia Louise Wyngaard, Kaukauna, WI (US); Heather S. Mortell, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 98 days.

(21) Appl. No.: 10/027,796

(22) Filed: Dec. 20, 2001

(65) Prior Publication Data
US 2003/0120252 A1    Jun. 26, 2003

(51) Int. Cl.
*A61F 13/15*    (2006.01)
*A61F 13/20*    (2006.01)

(52) U.S. Cl. .................................. 604/396; 604/385.01

(58) Field of Classification Search ........... 604/385.21, 604/396, 385.31, 392; 2/275, 274, 244; D24/124, D24/126; 156/73.4
See application file for complete search history.

(56) References Cited

U.S. PATENT DOCUMENTS

| | | | |
|---|---|---|---|
| 1,314,799 A * | 9/1919 | Guinzburg | 2/400 |
| 1,458,082 A * | 6/1923 | Stein | 2/400 |
| 1,491,528 A * | 4/1924 | Guinzburg | 2/400 |
| 2,164,036 A * | 6/1939 | Lane | 112/415 |
| 2,406,830 A * | 9/1946 | Haman et al. | 428/104 |
| 2,834,347 A | 5/1958 | Connally | |
| 3,338,992 A | 8/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,137,634 A * | 2/1979 | Klamar | 33/12 |
| 4,196,355 A * | 4/1980 | Maine | 250/516.1 |
| 4,205,679 A | 6/1980 | Repke et al. | |
| 4,224,740 A * | 9/1980 | Gibson | 33/17 A |
| 4,340,563 A | 7/1982 | Appel et al. | |
| 4,530,868 A | 7/1985 | Shinmi et al. | |
| 4,569,870 A * | 2/1986 | Shinmi | 428/57 |
| 4,610,681 A | 9/1986 | Strohbeen et al. | |
| 4,646,362 A | 3/1987 | Heran et al. | |
| 4,663,220 A | 5/1987 | Wisneski et al. | |
| 4,704,116 A | 11/1987 | Enloe | |

(Continued)

FOREIGN PATENT DOCUMENTS

EP    0 217 032    4/1987

(Continued)

OTHER PUBLICATIONS

Vogue Pattern 9631, "Seam Allowances", Copyright 1997.*

*Primary Examiner*—Karin Reichle
(74) *Attorney, Agent, or Firm*—Pauley Petersen & Erickson

(57) ABSTRACT

A personal care garment having side seams with a discreet or aesthetically pleasing appearance. The side seams can extend from a waist opening to each of two leg openings between a front side panel and a back side panel. In one embodiment, a ribbon cover is attached to an outer surface of the garment to secure the side seam and provide a finished, aesthetically pleasing appearance. In another embodiment, an embossing pattern can be applied to the side seam to provide a finished, aesthetically pleasing appearance.

12 Claims, 7 Drawing Sheets

U.S. PATENT DOCUMENTS

| | | | |
|---|---|---|---|
| 4,747,846 A * | 5/1988 | Boland et al. | 604/385.22 |
| 4,753,182 A * | 6/1988 | Blackburn | 112/419 |
| 4,803,109 A * | 2/1989 | Saniscalchi | 428/104 |
| 4,909,804 A | 3/1990 | Douglas, Sr. | |
| 4,920,575 A * | 5/1990 | Bartasis et al. | 2/457 |
| 4,932,078 A * | 6/1990 | Jones et al. | 2/70 |
| 4,938,757 A * | 7/1990 | Van Gompel et al. | 604/396 |
| 4,938,817 A * | 7/1990 | Langley | 156/73.1 |
| 4,940,464 A | 7/1990 | Van Gompel et al. | |
| 5,046,272 A | 9/1991 | Vogt et al. | |
| 5,074,854 A | 12/1991 | Davis | |
| 5,104,116 A | 4/1992 | Pohjola | |
| 5,163,932 A | 11/1992 | Nomura et al. | |
| 5,224,405 A | 7/1993 | Pohjola | |
| 5,226,992 A | 7/1993 | Morman | |
| 5,232,529 A * | 8/1993 | Miyake | 156/73.4 |
| 5,236,430 A | 8/1993 | Bridges | |
| 5,246,433 A | 9/1993 | Hasse et al. | |
| 5,531,732 A * | 7/1996 | Wood | 604/391 |
| 5,569,234 A | 10/1996 | Buell et al. | |
| 5,569,507 A * | 10/1996 | Goodwin et al. | 728/76 |
| 5,603,123 A * | 2/1997 | Chupa | 2/275 |
| 5,618,366 A | 4/1997 | Suekane | |
| 5,635,290 A * | 6/1997 | Stopper et al. | 428/198 |
| 5,662,638 A | 9/1997 | Johnson et al. | |
| 5,786,058 A | 7/1998 | Megchelsen et al. | |
| 5,876,394 A * | 3/1999 | Rosch et al. | 604/393 |
| 5,885,679 A * | 3/1999 | Yasue et al. | 428/57 |
| 5,919,539 A * | 7/1999 | Bisbis et al. | 428/57 |
| 6,120,489 A | 9/2000 | Johnson et al. | |
| 6,149,637 A * | 11/2000 | Allen et al. | 604/366 |
| 6,302,871 B1 | 10/2001 | Nakao et al. | |
| 6,387,994 B1 * | 5/2002 | Gore et al. | 524/198 |
| 6,497,934 B1 * | 12/2002 | Mahn et al. | 428/57 |
| 2003/0120254 A1 * | 6/2003 | Franke et al. | 604/396 |

FOREIGN PATENT DOCUMENTS

| | | |
|---|---|---|
| EP | 0 635 248 A1 | 1/1995 |
| GB | 2 046 171 | 11/1980 |
| GB | 2071564 A * | 9/1981 |
| GB | 2215660 A * | 9/1989 |
| WO | WO 9107278 A1 * | 5/1991 |
| WO | WO 9616220 A1 * | 5/1996 |
| WO | 99/60966 | 12/1999 |
| WO | 99/60971 | 12/1999 |
| WO | 00/35395 | 6/2000 |
| WO | WO 200126495 A1 * | 4/2001 |
| WO | 01/91992 | 12/2001 |

* cited by examiner

AESTHETICALLY IMPROVED SIDE PANELS FOR DISPOSABLE GARMENT AND METHODS OF MAKING THE SAME

FIELD OF THE INVENTION

This invention is directed to discreet or concealed side seams for a pant-like disposable garment having an aesthetically pleasing appearance.

BACKGROUND OF THE INVENTION

Disposable garments, such as adult incontinence wear as well as infant and children's diapers, swim wear and training pants, typically have a front side panel and a back side panel which are joined together at a side seam to provide a complete side panel. The side panels are typically connected at the side seam using a conventional ultrasonic process. Often, the resulting side seam and edge portions of the front side panel and back side panel protrude outwardly from the side of the garment, and can make the side seam appear unfinished or less garment-like.

There is a need or desire for disposable garments that have side seams which reduce the amount of side panel material that protrudes outwardly from the side of the garment after the front side panel is bonded to the back side panel.

There is a need or desire for disposable garments that have side seams which connect the front side panel and back side panel together and provide a more aesthetically pleasing appearance.

There is a need or desire for disposable garments that include means for covering the side seams which connect the front side panel and back side panel together to provide a more aesthetically pleasing appearance.

SUMMARY OF THE INVENTION

The present invention is directed to disposable garments having side seams which connect a front side panel to a back side panel to form a complete side panel which has an aesthetically pleasing appearance. Several bonding patterns can be used to produce absorbent garments having side seams with reduced side panel material protruding from a side of the garment to provide a more aesthetically pleasing side seam. In one embodiment of this invention, a ribbon cover is applied to an outer surface of the side seam to secure the side seam as well as conceal the side seam and provide a finished, aesthetically pleasing appearance. Alternatively or in addition to the ribbon cover, a decorative embossing pattern can be applied to at least an outer surface of the side seam to provide a finished, aesthetically pleasing appearance.

Each side seam includes an edge portion of a front side panel and an edge portion of a back side panel. The edge portions are bonded together using a bonding pattern which provides a primary bond. The side seams can extend from a waist opening to each of two leg openings between a front side panel and a back side panel. The ribbon cover can be attached and/or the embossing pattern can be applied to the side seam to provide the aesthetically pleasing appearance.

With the foregoing in mind, it is a feature and advantage of the invention to provide a discreet or concealed side seam for a disposable garment that has an aesthetically pleasing appearance.

DEFINITIONS

Figure 1:
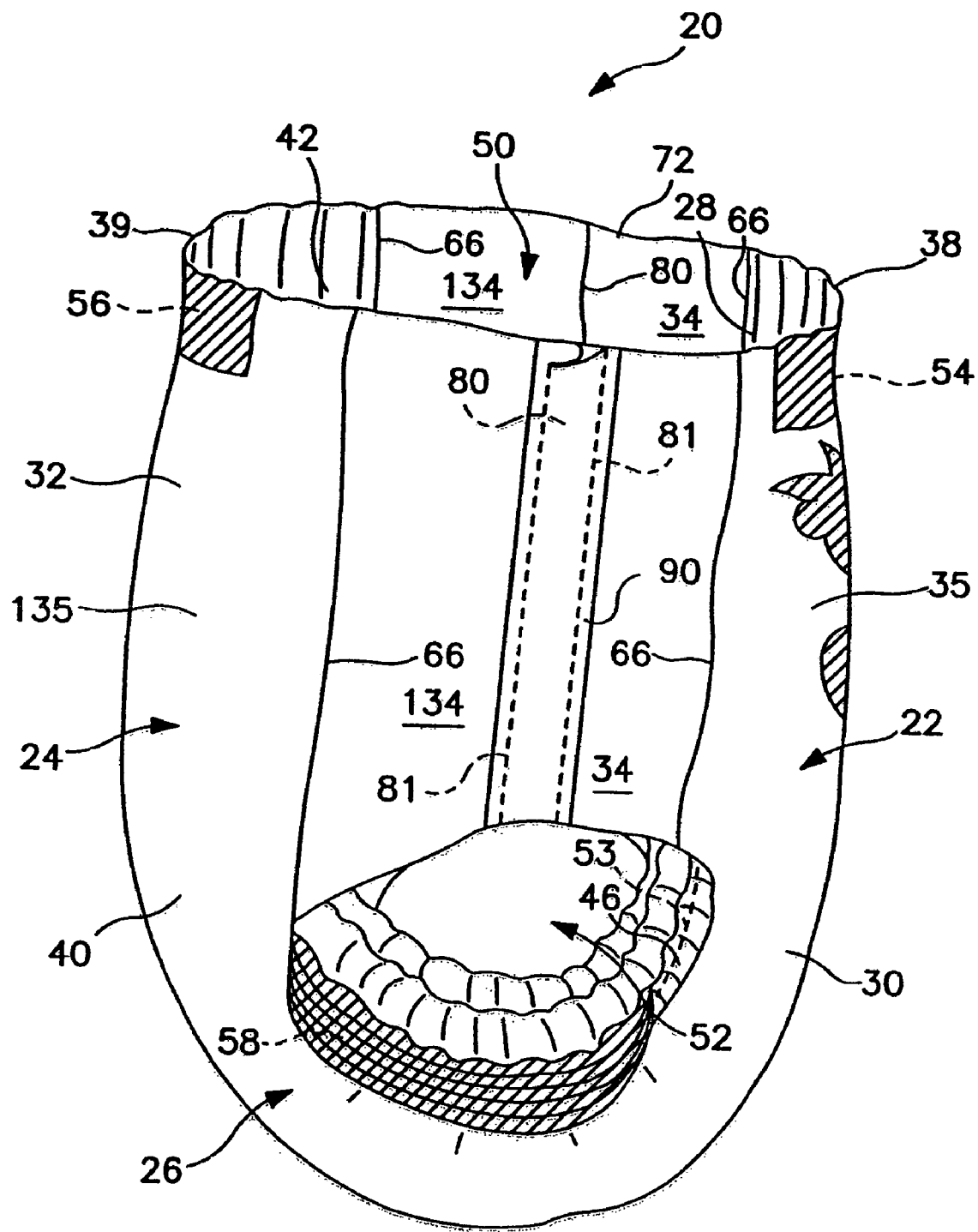
FIG. 1 is a side perspective view of an absorbent garment having side seams covered by a ribbon cover, according to one embodiment of this invention.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Cross direction" refers to the width of a fabric in a direction generally perpendicular to the direction in which it is produced, as opposed to "machine direction" which refers to the length of a fabric in the direction in which it is produced.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flexible" refers to materials which are compliant and which will readily conform to the general shape and contours of the wearer's body.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 3:
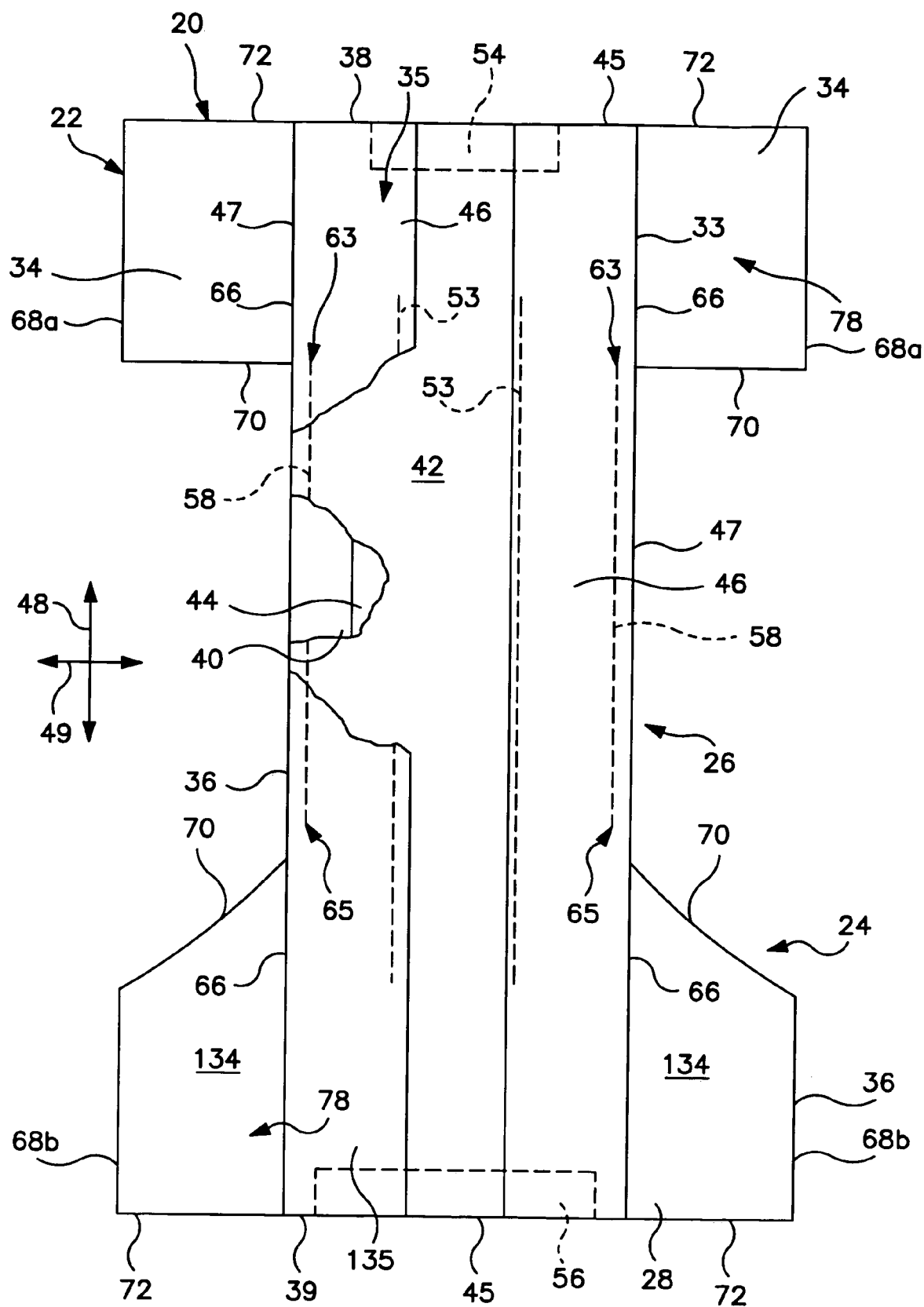
FIG. 3 is a plan view of the absorbent garment of FIGS. 1 and 2 in a partially disassembled, stretched flat state, and showing the surface of the garment that faces the wearer when the article is worn, and with portions cut away to show the underlying features, according to one embodiment of this invention.

"Longitudinal" and "transverse" have their customary meaning, as indicated by the longitudinal and transverse axes depicted in FIG. 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Machine direction" refers to the length of a fabric in the direction in which it is produced, as opposed to "cross direction" which refers to the width of a fabric in a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Ribbon cover" refers to a material which covers or is laid over a bonding area wherein a substrate or a plurality of substrates are bonded such that the bonding area is not visible. Desirably, the ribbon cover is bonded to at least one substrate in a bonding area using suitable bonding means, for example adhesive bonding or ultrasonic bonding. The ribbon cover may be made of a material that is similar to the substrate material or a material that is different from the substrate material.

"Side seam" refers to a region on a pant-like disposable garments, such as a personal care garment, where a front side panel is connected to a back side panel.

"Shearing strain" refers to forces that tend to produce an opposite but parallel sliding motion between two bodies' planes.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE INVENTION

The present invention is directed to a disposable garment having means for covering a side seam connecting a front side panel to a rear side panel. In one embodiment of this invention, a ribbon cover can be bonded to and cover at least a portion of the side seam connecting the front side panel and the back side panel together to secure the side seam and provide a finished or aesthetically pleasing appearance. Alternatively, or in addition to the ribbon cover, a decorative embossing pattern, desirably an ultrasonic embossing pattern, may be applied to the side seam.

The principles of the present invention can be incorporated into any suitable disposable article. Examples of such suitable articles include absorbent garments such as diapers, training pants, feminine hygiene products, incontinence products, as well as other personal care garments, disposable clothing, health care garments, or the like. For ease of explanation, the description hereafter will be in terms of a child's training pant.

Referring to FIG. 1, a disposable absorbent article, such as a training pant 20, is illustrated in a fastened condition. The training pant 20 includes an absorbent chassis 32. The absorbent chassis 32 defines a front region 22, a back region 24, a crotch region 26 interconnecting the front region 22 and the back region 24, an inner surface 28 which is configured to contact the wearer, and an outer surface 30 opposite the inner surface 28 which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

Figure 2:
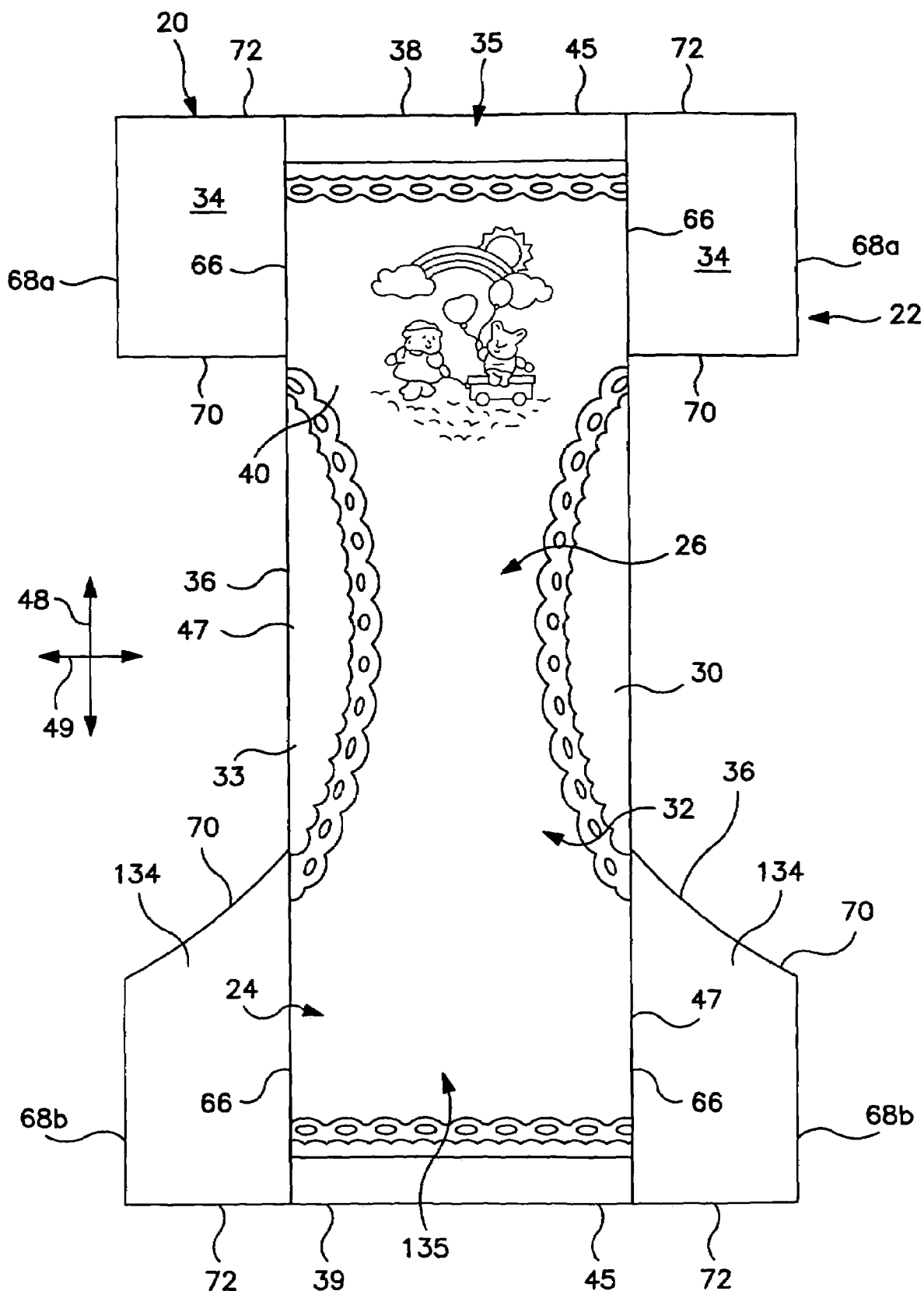
FIG. 2 is a plan view of the absorbent garment of FIG. 1 in a partially disassembled, stretched flat state, and showing the surface of the garment that faces away from the wearer when the garment is worn, according to one embodiment of this invention.

The illustrated absorbent chassis 32 can include a somewhat rectangular composite structure 33, a pair of transversely opposed front side panels 34, and a pair of transversely opposed back side panels 134. The composite structure 33 and side panels 34 and 134 may be integrally formed (not shown) or may include two or more separate elements, as shown in FIGS. 2 and 3. The illustrated composite structure 33 includes an outer cover 40, a bodyside liner 42 which is connected to the outer cover in a superposed relation, an absorbent assembly 44 (FIG. 3) which is located between the outer cover 40 and the bodyside liner 42, and a pair of containment flaps 46 (FIG. 3). The rectangular composite structure 33 has opposite linear end edges 45 that form portions of the front and back waist edges 38 and 39, and opposite linear or curvilinear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as illustrated in FIG. 1, the front region 22 and the back region 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front side panels 34 and the back side panels 134 include the portions of the training pant 20 which, when worn, are positioned on the hips of the wearer.

The front region 22 of the absorbent chassis 32 includes the transversely opposed front side panels 34 and a front center panel 35 (FIGS. 1–3) positioned between and interconnecting the side panels, along with a front waist elastic member 54 and any other connected components. The back region 24 of the absorbent chassis 32 includes the transversely opposed back side panels 134 and a back center panel 135 (FIGS. 2 and 3) positioned between and interconnecting the side panels, as well as a rear waist elastic member 56 and any other connected components. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably, although not necessarily, includes the pair of containment flaps 46 which are configured to provide a barrier to the transverse flow of body exudates. A flap elastic member 53 (FIGS. 1 and 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis 32 or may only extend partially along the length of the absorbent chassis 32. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes the front waist elastic member 54, the rear waist elastic member 56, and leg elastic members 58, as are known to those skilled in the art (FIGS. 1 and 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbond web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL -62 from Uniqema Inc., a division of ICI of New Castle, Del. U.S.A. and GLUCOPON 220UP from Cognis Corporation of Ambler, Pa. and produced in Cincinnati, Ohio, in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) is positioned between the outer cover 40 and the bodyside liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the composite structure 33 of the absorbent chassis 32 in the respective front and back regions 22 and 24, and are attached or connected to one another at a side seam 80. The front side panel 34 and back side panel 134 can be releasably attached or can be permanently bonded together. More particularly, as shown best in FIGS. 2 and 3, the front side panels 34 can be permanently bonded to and extend transversely beyond the side edges 47 of the composite structure 33 in the front region 22 along attachment lines 66, and the back side panels 134 can be permanently bonded to and extend transversely beyond the side edges of the composite structure in the back region 24 along attachment lines 66. The side panels 34 and 134 may be attached to the composite structure 33 and to each other using attachment means known to those skilled in the art such as adhesive bonding, thermal bonding or ultrasonic bonding. The side panels 34 and 134 can also be formed as a portion of a component of the composite structure 33, such as the outer cover 40 or the bodyside liner 42.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to a distal edge 68b of the back panel 134, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis 49 of the training pant 20. In particular embodiments, the front and back side panels 34 and 134 may each include an interior portion 78 disposed between the distal edge 68a, 68b and the respective front or back center panel 35 or 135. In the illustrated embodiment in FIG. 3, the interior portions 78 are disposed between the distal edges 68a, 68b and the side edges 47 of the rectangular composite structure 33. The elastic material of the side panels 34 and 134 can be disposed in the interior portions 78 to render the side panels elastomeric in a direction generally parallel to the transverse axis 49. Most desirably, each side panel 34 and 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

As shown in FIG. 1, the training pant 20 according to the present invention includes a pair of laterally opposing side seams 80 for securing each front side panel 34 to the corresponding back side panel 134. Suitably, the side seam 80 has a width of less than about 10 mm, desirably about 2 mm to about 8 mm. In alternative embodiments, the side seam 80 may have a greater width, for example up to about 30 mm. Further, the side seam 80 desirably extends from the waist opening 50 to one leg opening 52 between the front side panel 34 and the back side panel 134. In an alternative embodiment, the side seams 80 extend along a portion of the side panels 34 and 134 between the waist opening 50 and the leg openings 52.

Figure 4A:
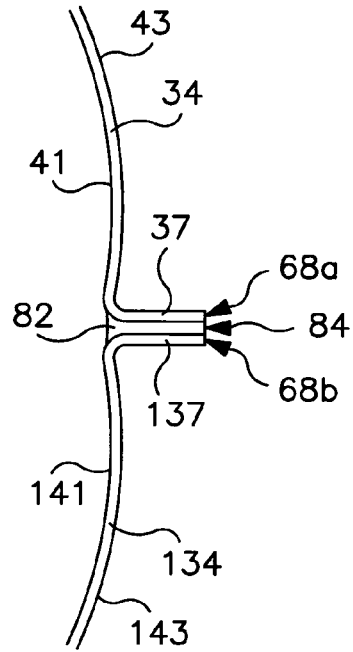
FIG. 4A illustrates a cross-sectional view of a prior art butt seam.

As shown in FIGS. 4A–6, the front side panel 34 is connected to the back side panel 134 at the side seam 80 using conventional bonding means, such as adhesive bonding and/or ultrasonic bonding means. For example, as shown in FIG. 4A, a first or primary bond 82 connects an edge portion 37 of the front side panel 34 to an edge portion 137 of the corresponding back side panel 134 to form a standing butt seam 84 between the front side panel 34 and the rear side panel 134. More specifically, an inner surface 41 of the front side panel 34 at the edge portion 37 is bonded to an inner surface 141 of the back side panel 134 at the edge portion 137. Any suitable bonding means known to those having ordinary skill in the art can be used to bond the inner surface 41 to the inner surface 141. Desirably, the primary bond 82 is an adhesive bond, an ultrasonic bond or a combination thereof. In one embodiment, the primary bond 82 may have a width of about less than about 10 mm, desirably about 2 mm to about 8 mm. In alternative embodiments, the primary bond may have a greater width, for example a width of about 30 mm.

As used herein, the term "standing butt seam" refers to a seam wherein two separate pieces of substrate are bonded together face-to-face or back-to-back in close proximity to an outer edge of each of the pieces of substrate, and the outer edges of the pieces of substrate project outward from the finished product, placing the standing butt seam 84 in peel, as opposed to shearing strain. Excess side panel material near the standing butt seam 84 area, if any, can be trimmed or removed such that the edge portions 37, 137 are coterminous.

Figure 4B:
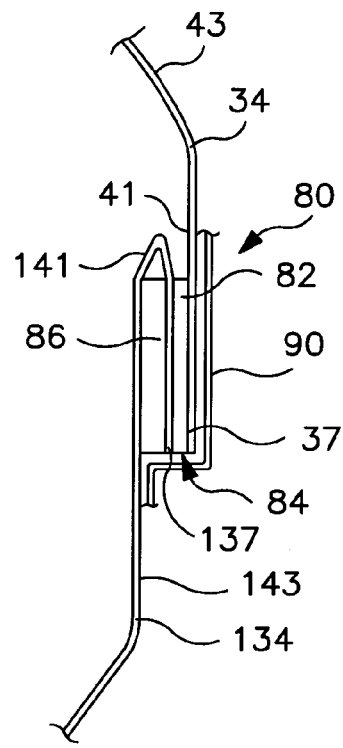
FIG. 4B illustrates a cross-sectional view of a ribbon cover bonded to a side seam to secure and conceal the side seam and provide an aesthetically pleasing appearance, according to one embodiment of this invention.

Referring to FIG. 4B, the standing butt seam 84 can be folded flat with respect to an outer surface 143 of the back side panel 134 so that the standing butt seam 84 is visible and generally parallel to the outer surface 143. The standing butt seam 84 can be bonded to the outer surface 143 of the back side panel 134 using a second or secondary bond 86, as shown in FIG. 4B, thus, forming the side seam 80. The secondary bond 86 may include any suitable bond, such as an adhesive bond and/or an ultrasonic bond and desirably, but not necessarily, may have a width about equal to, wider or narrower than the primary bond 82. Alternatively, the standing butt seam 84 can be folded flat with respect to an outer surface 43 of the front side panel 34 and bonded thereto to form the side seam 80.

Figure 5:
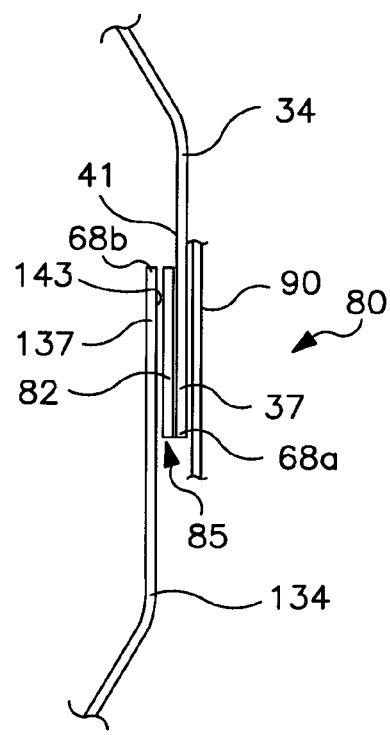
FIG. 5 illustrates a cross-sectional view of a ribbon cover bonded to a side seam to secure the side seam and provide an aesthetically pleasing appearance, according to one embodiment of this invention.

In one embodiment of this invention as shown in FIG. 5, the primary bond 82 connects the edge portion 37 of the front side panel to the edge portion 137 of the corresponding back side panel 134 to form a lap side seam 85, as shown in FIG. 5. The term "lap side seam," as used herein, refers to a seam connecting the front side panel 34 and the back side panel 134 such that the front side panel 34 and the back side panel 134 overlap and the side seam 80 is located between the distal edges 68a of the front side panel 34 and the distal edge 68b of the back side panel 134. The lap side seams 85 experience a shearing strain during use, as opposed to peel forces, thereby reducing the likelihood of the seams opening unexpectedly.

The edge portions 37 and 137 can be overlapped sufficiently to allow the primary bond 82 to attach the side panels 34 and 134 together. Suitably, the front side panel 34 overlaps the back side panel 134 by a distance of less than about 30 mm, desirably about 2 mm to about 8 mm, still more desirably about 2 mm to about 6 mm. More specifically, an inner surface 41 of the front side panel 34 at the edge portion 37 is bonded to an outer surface 143 of the back side panel 134 at the edge portion 137. The overlap orientation provides a side seam 80 which does not have to be trimmed after the bonding process and, thus, reduces the material needed and the material wasted to produce side panels 34 and 134. Further, the overlap orientation limits the material which protrudes outwardly from a lateral surface of the training pant 20, after the side seam 80 is formed.

Figure 6A:
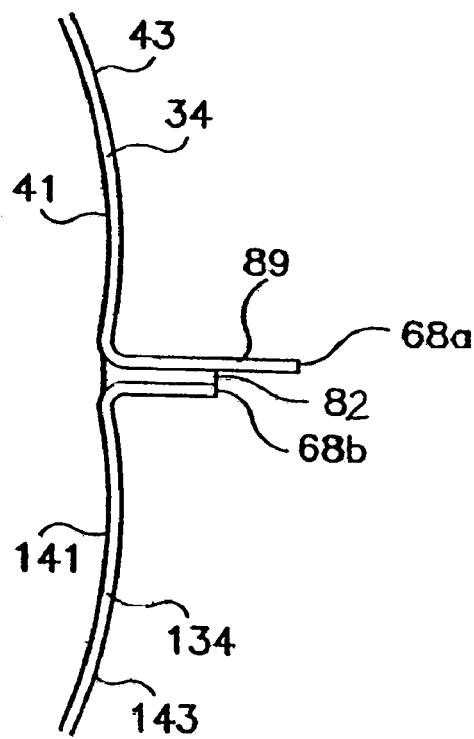
FIGS. 6A and 6B illustrate a cross-sectional view of a ribbon cover bonded to a side seam to secure and conceal the side seam and provide an aesthetically pleasing appearance, according to one embodiment of this invention.
Figure 6B:
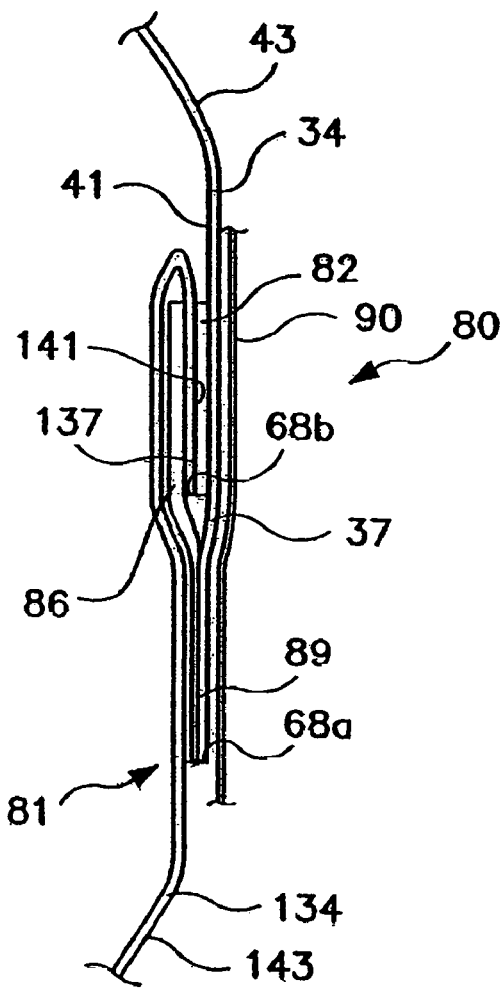

In one embodiment of this invention as shown in FIGS. 6A and 6B, the primary bond 82, in combination with the secondary bond 86 discussed below, connects the inner surface 41 of the edge portion 37 of the front side panel 34 to the inner surface 141 of the edge portion 137 of the corresponding back side panel 134 to form an "offset butt side seam." The term "offset butt side seam," as used herein, refers to a seam connecting the front side panel 34 and the back side panel 134 such that the front side panel 34 and the back side panel 134 are bonded together face-to-face or back-to-back at the primary bond 82 in close proximity to a distal edge 68a, 68b of each of the side panels 34 and 134 such that an offset portion of one of the front side panel 34 and the back side panel 134 extends in a lateral direction outwardly from the primary bond 82.

In this embodiment, one of the front side panel 34 and the back side panel 134 is longer than the other side panel in a cross direction or lateral direction of the training pant 20. For example, as shown in FIG. 6A, the front side panel 34 is longer in the cross direction than the back side panel 134 to form the offset portion 89 of the front side panel 34, which can be bonded to the outer surface 143 of the back side panel 134 by the secondary bond 86, as discussed below. Desirably, the offset portion 89 has a length in the cross direction of about 2 mm to about 10 mm, more desirably about 3 mm to about 8 mm. In alternative embodiments, the offset portion 89 may be as wide as about 30 mm.

The inner surface 41 of the edge portion 37 is bonded to the inner surface 141 of the edge portion 137 at a laterally inward distance from the distal edge 68a such that the distance between the distal edge 68a of the front side panel and the distal edge 68b of the back side panel is equal to the length of the offset portion 89. Desirably, the primary bond 82 is an adhesive bond or an ultrasonic bond and is positioned within about 15 mm from the distal edge 68b, for example about 4 mm from the distal edge 68b. The primary bond 82 desirably extends inwardly about 2 mm to about 30 mm, more desirably about 2 mm to about 8 mm. The primary bond 82 may also be positioned such that it extends outwardly over the distal edge 68b of the back side panel 134 up to about 20 mm. The primary bond 82 desirably extends inwardly up to about 30 mm.

Referring to FIG. 6B, the edge portion 137 can be folded flat with respect to the outer surface 143 of the back side panel 134 such that the front side panel 34 covers the edge portion 137 of the back side panel 134 and the outer surface 143 is in facing relationship with the inner surface 41 of the front side panel 34 at the offset portion 89. The offset portion 89 can be bonded to the outer surface 143 by the secondary bond 86, as shown in FIG. 6B. The secondary bond 86 desirably, but not necessarily, extends from the front distal edge 68a to the back distal edge 68b. This secondary bond 86 may also extend about 1 mm to about 12 mm on either side (distal or proximal) of the front distal edge 68a and the back distal edge 68b. The edge portion 137 can be bonded to the folded over portion of the edge portion 137, thus, forming the side seam 80. The secondary bond 86 can include any suitable bond, such as an adhesive bond and/or an ultrasonic bond.

In an alternative embodiment of this invention, the back side panel 134 can be offset from the front side panel 34 and the offset portion 89 of the back side panel 134 can be bonded by the secondary bond 86 to the outer surface 43 of the front side panel 34 at the edge portion 37, after the front side panel 34 is folded so that the outer surface 43 of the front side panel 34 is in facing relationship with the inner surface 141 of the back side panel 134.

Desirably, a covering means is provided to cover at least a portion of the side seam 80 for improving the aesthetics of the side seam 80. In one embodiment of this invention, a ribbon cover 90 can be attached or connected to at least a portion of the training pant 20, as shown in FIGS. 4A–6B. In one embodiment of this invention, the ribbon cover 90 may be connected to at least a portion of the side seam 80. Further, the ribbon cover 90 covers at least a portion of the side seam 80 to provide a finished, aesthetically pleasing appearance, providing a continuous or uniform appearance across the corresponding side panels 34 and 134.

The ribbon cover 90 desirably has a width sufficient to cover the width of the side seam 80. Alternatively, the ribbon cover 90 may have a width that covers only part of the width of the side seam 80, such as a seam junction that appears on the outer surface of the garment. Desirably, but not necessarily, the ribbon cover 90 covers the width of the side seam 80 such that a portion of the ribbon cover 90 extends beyond each side edge 81 of the side seam 80 onto the outer surface of the side panels 34 or 134. Desirably, if the ribbon cover 90 covers the entire side seam 80, the ribbon cover 90 may extend beyond each side edge 81 of the side seam 80 by about 0 mm to about 15 mm. Accordingly, the ribbon cover 90 can have any suitable width, such as about 5 mm to about 50 mm, more desirably about 7 mm to about 15 mm. Further, the ribbon cover 90 desirably, although not necessarily, has a length sufficient to cover the side seam 80 along its length. For example, if the side seam 80 as shown in FIG. 1 extends from the waist opening 50 to the leg opening 52, the ribbon cover 90 desirably extends from the waist opening 50 to the leg opening 52. In one embodiment of this invention, a portion of the ribbon cover 90 extends past the waist edge 72 and/or the leg edge 70 of the side panels 34 and 134. The portion which extends over the edges of the side panels 34 and 134 can be folded over the respective edge and bonded to an inner surface of the side panels 34 and/or 134 (not shown).

Desirably, but not necessarily, the ribbon cover 90 is bonded to the side seam 80 and/or the side panels 34, 134 using ultrasonic bonds. It is apparent to those having ordinary skill in the art that any suitable bonding means can be used to bond the ribbon cover 90 to the side seam 80 and/or the side panels 34, 134. In one embodiment of this invention, the ribbon cover 90 can be embossed for aesthetic purposes to present an aesthetically pleasing appearance. Desirably, but not necessarily, the ribbon cover 90 is embossed prior to being bonded to the side seam 80 and/or the side panels 34, 134. In alternative embodiments, the embossing application can also bond the ribbon cover 90 to side seam 80 and/or the side panels 34, 134.

Materials suitable for use as the ribbon cover 90 include any material that will sufficiently cover the side seam 80 and provide the desired levels of flexibility and softness, for example any nonwoven material, including those materials suitable for use as the side panels 34 and 134, discussed above. Desirably, although a not necessarily, the material used for the ribbon cover 90 has similar flexibility, appearance and softness as the side panel materials. As such, the ribbon cover 90 can blend with the side panels 34 and 134 to provide an appearance of uniformity across the complete side panel. The material can in particular embodiments have sufficient opacity and thickness to conceal the side seam 80. The material may have any suitable thickness, for example a thickness obtained with a material having a basis weight of about 0.4 osy to about 0.8 osy. The ribbon cover 90 should be non-irritating and may be breathable or non-breathable.

In one embodiment of this invention, the ribbon cover 90 is tearable such that the ribbon cover 90 can be peeled off the side seam 80 and in the process open the side seam 80 to release the front side panel 34 from the back side panel 134.

In one embodiment of this invention, a decorative embossing pattern 100 can be applied to at least a portion of the side seam 80, as shown in FIGS. 7–10. The decorative embossing pattern 100 covers at least a portion of the side seam 80 to provide a finished, aesthetically pleasing appearance, providing a continuous or uniform appearance across the corresponding side panels 34 and 134. The embossing pattern 100 may be applied to the side seam 80 in addition to the cover ribbon 90 or in lieu of the cover ribbon 90. In certain embodiments, the embossing pattern 100 may assist in connecting the front and back side panels 34 and 134.

For example, a standing butt seam 84, as shown in FIG. 4A, can be formed between the front side panel 34 and the rear side panel 134, using bonding means such as adhesive or ultrasonic bonding means. The standing butt seam 84 can then be folded over onto a portion of the front side panel 34 or the rear side panel 134 and bonded thereto using suitable bonding means such as an adhesive, to form a training pant 20 in an assembled pant-like configuration. Referring to FIG. 7-10, the assembled training pant 20 can be run through an ultrasonic unit or other suitable embossing device to emboss an area on each side of the training pant 20 to form the embossing pattern 100 which covers or hides at least a portion of the side seam 80.

Desirably, the ultrasonic embossing pattern 100 has a depth that is visible and well defined but does not burn or produce holes in the side seam 80. The depth of the ultrasonic embossing pattern 100 is dependent upon several factors, including the type of material used to make the side panels 34 and 134, and the basis weight of the material.

Figure 7:
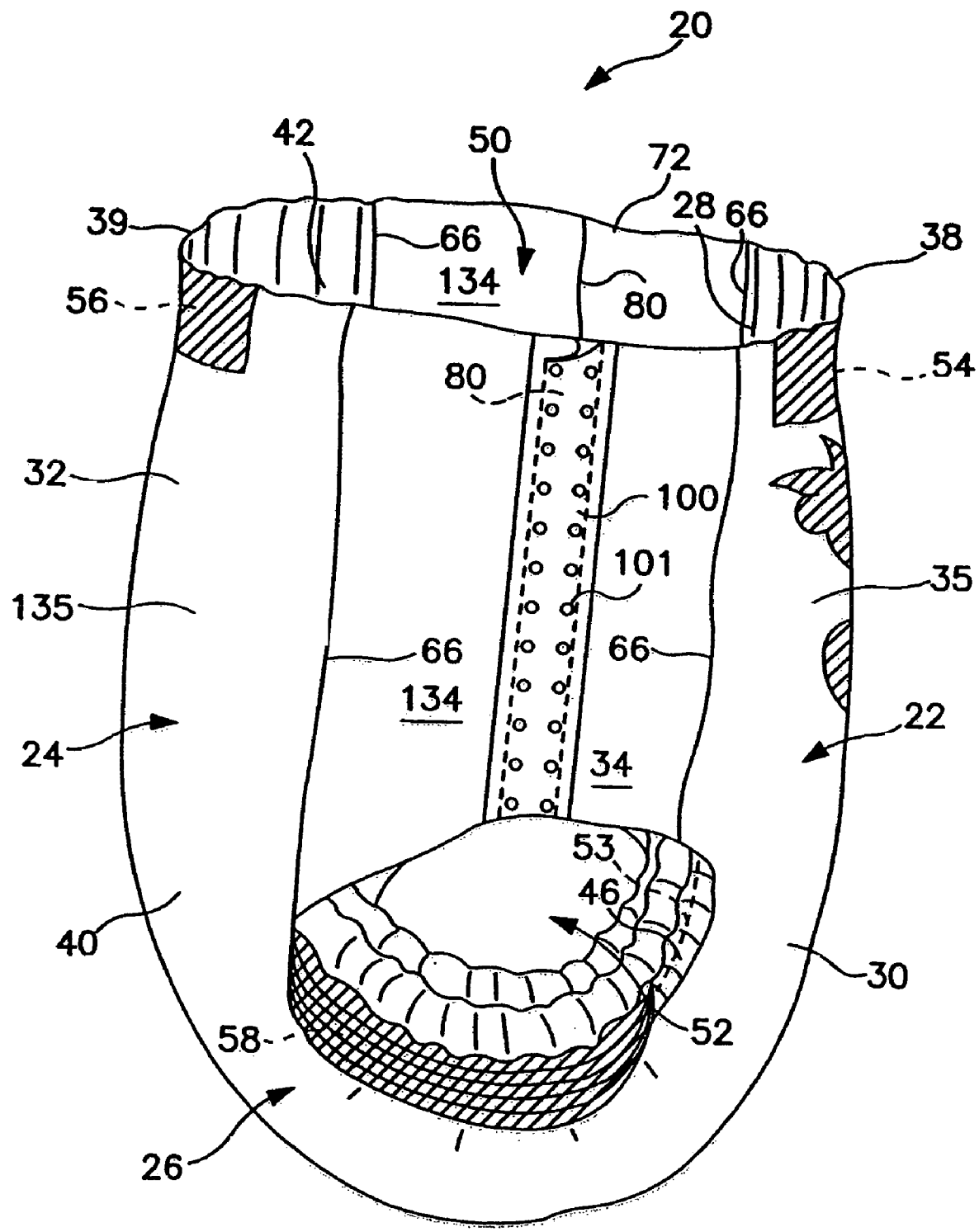
FIG. 7 is a side perspective view of an absorbent garment having side seams covered by an embossing pattern, according to one embodiment of this invention.

The embossing pattern 100 desirably, although not necessarily, has a width sufficient to cover the width of the side seam 80. Desirably, but not necessarily, the embossing pattern 100 covers the width of the side seam 80 such that a portion of the embossing pattern 100 extends beyond each side edge of the side seam 80 onto the outer surface of the side panels 34 or 134. Desirably, the embossing pattern 100 extends about 0 to about 15 mm, for example about 2 mm to about 4 mm, beyond each side edge of the side seam 80. For example, the width of the embossing pattern 100 desirably is about 4 mm to about 40 mm, more desirably about 7 mm to about 15 mm. Further, the embossing pattern 100 desirably, although not necessarily, has a length sufficient to cover the side seam 80 along its length. For example, if the side seam 80 as shown in FIG. 7 extends from the waist opening 50 to the leg opening 52, the embossing pattern 100 desirably extends from the waist opening 50 to the leg opening 52.

Figure 8:
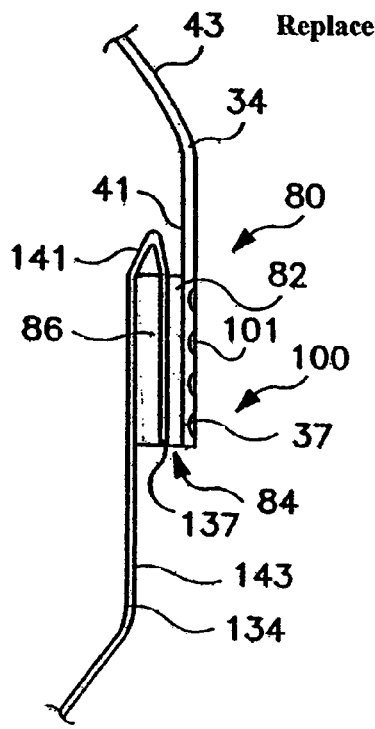
FIG. 8 illustrates a cross-sectional view of an embossing pattern covering a side seam to provide an aesthetically pleasing appearance, according to one embodiment of this invention.
Figure 9:
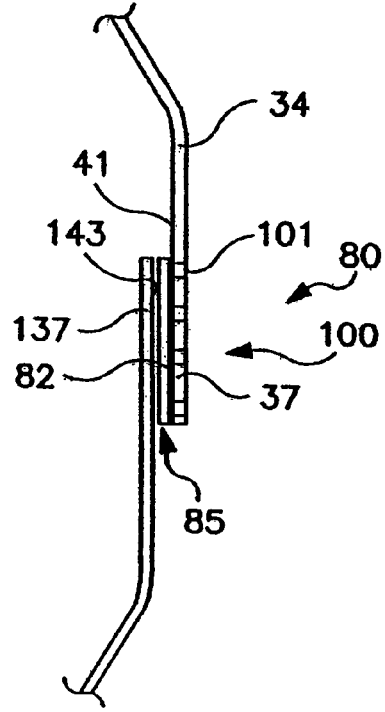
FIG. 9 illustrates a cross-sectional view of an embossing pattern covering a side seam to provide an aesthetically pleasing appearance, according to one embodiment of this invention.
Figure 10:
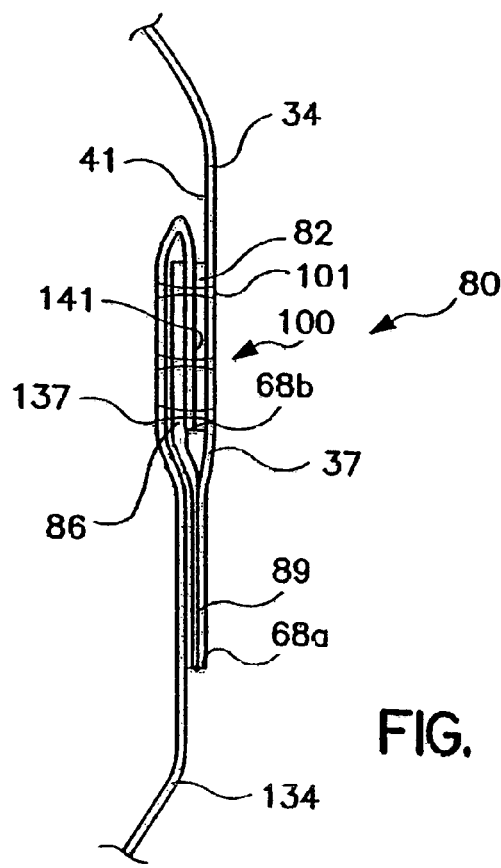
FIG. 10 illustrates a cross-sectional view of an embossing pattern covering a side seam to provide an aesthetically pleasing appearance, according to one embodiment of this invention.

Referring to FIGS. 8–10, in one embodiment of this invention the embossing pattern 100 includes a plurality of embossing dimples 101 which penetrate a surface of an outer layer of the side seam 80. The embossing dimples 101 can penetrate through only a portion of the outer layer (FIG. 8), through at least one layer (FIG. 9) or through all layers of the side seam 80 (FIG. 10). Thus, the embossing dimples 101 do not necessarily penetrate through each layer of the side seam 80. The primary bond 82 and the secondary bond 86 provide strength for the side seam 80, while the embossing pattern 100 may provide a decorative aesthetic pattern to cover the side seam 80. Desirably, the embossing dimples have a suitable depth, which depends upon the materials being used to form each side panel 34, 134 and the number of layers which the embossing dimples penetrate. The embossing pattern 100 may produce an embossing pattern wherein the embossing dimples 101 have varying depths or dimensions. Such depths and dimensions can be varied by varying the nip pressure and/or the power of the ultrasonic unit. In one embodiment of this invention, the embossing pattern 100 is tearable such that the side seam 80 tears to release the front side panel 34 from the back side panel 134.

As described herein, the various components of the training pant 20 can be integrally assembled together employing various types of suitable attachment means, such as adhesive, sonic and thermal bonds or combinations thereof. The resulting product is a garment having side seams connecting corresponding front side panels and back side panels, and a ribbon cover which secures the side seam and provides a finished or aesthetically pleasing appearance.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A personal care garment comprising:
    a front waist region, a back waist region, and a crotch region extending between the waist regions;
    a first side panel extending from the front waist region;
    a second side panel extending from the back waist region;
    a side seam connecting an inner surface of an edge portion of the first side panel to an inner surface of an edge portion of the second side panel, the edge portion of the second side panel folded flat with respect to and bonded directly to an outer surface of the second side panel; and
    a ribbon cover laid over the side seam and covering the side seam, the ribbon cover having a first edge portion bonded directly to an outer surface of the first side panel and a second edge portion bonded directly to the outer surface of the second side panel, the ribbon cover having a width of about 5 mm to about 50 mm;
    wherein the personal care garment is disposable and comprises at least one of the group consisting of diapers, training pants, feminine hygiene products, and incontinence products.

2. The personal care garment of claim 1 wherein the side seam has a width of less than about 30 mm.

3. The personal care garment of claim 1 wherein the side seam has a width of about 2 mm to about 10 mm.

4. The personal care garment of claim 1 wherein the side seam has a width of about 3 mm to about 5 mm.

5. The personal care garment of claim 1 wherein the ribbon cover has a width of about 7 mm to about 15 mm.

6. The personal care garment of claim 1 wherein the ribbon cover extends beyond a side edge of the side seam at least about 2 mm.

7. The personal care garment of claim 1 wherein the ribbon cover extends beyond a side edge of the side seam about 0 mm to about 15 mm.

8. The personal care garment of claim 1 wherein the ribbon cover is bonded ultrasonically.

9. A disposable garment, comprising:
- a chassis comprising a front waist region and a back waist region, and defining a waist opening and first and second leg openings;
- an absorbent core within the chassis;
- a first side seam extending from the waist opening to the first leg opening connecting an inner surface of a first front side panel extending from the front waist region and an inner surface of a first back side panel extending from the back waist region;
- a first ribbon cover having a first edge portion bonded directly to an outer surface of the first front side panel and a second edge portion bonded directly to an outer surface of the first back side panel and extending from the waist opening to the first leg opening, the first ribbon cover covering the first side seam and having a width of about 5 mm to about 50 mm;
- a second side seam extending from the waist opening to the second leg opening connecting an inner surface of a second front side panel extending from the front waist region and an inner surface of a second back side panel extending from the back waist region; and
- a second ribbon cover having a first edge portion bonded directly to an outer surface of the second front side panel and a second edge portion bonded directly to an outer surface of the second back side panel and extending from the waist opening to the second leg opening, the second ribbon cover covering the second side seam and having a width of about 5 mm to about 50 mm.

10. The disposable garment of claim 9 wherein the front side panel and the back side panel, the first ribbon cover and the second ribbon cover each comprises an elastic material.

11. The disposable garment of claim 9 wherein the first ribbon cover and the second ribbon cover each comprises an elastic material.

12. The disposable garment of claim 9 wherein a width of the first ribbon cover is greater than a width of the first side seam and a width of the second ribbon cover is greater than a width of the second side seam.

* * * * *